(12) United States Patent
Wagner et al.

(10) Patent No.: US 6,985,281 B2
(45) Date of Patent: Jan. 10, 2006

(54) PACKAGE FOR OPTICAL COMPONENTS

(75) Inventors: Matthias Wagner, Cambridge, MA (US); Robert Murano, Malden, MA (US); Eugene Y. Ma, Chestnut Hill, MA (US); Steven Sherman, Boston, MA (US); Lawrence H. Domash, Conway, MA (US)

(73) Assignee: Aegis Semiconductor, Inc., Woburn, MA (US)

( * ) Notice: Subject to any disclaimer, the term of this patent is extended or adjusted under 35 U.S.C. 154(b) by 0 days.

(21) Appl. No.: 10/306,056

(22) Filed: Nov. 27, 2002

(65) Prior Publication Data

US 2003/0151818 A1 Aug. 14, 2003

Related U.S. Application Data

(60) Provisional application No. 60/335,178, filed on Nov. 28, 2001, and provisional application No. 60/394,500, filed on Jul. 9, 2002.

(51) Int. Cl.
*G02F 1/29* (2006.01)

(52) U.S. Cl. .................................. 359/315; 359/578
(58) Field of Classification Search ................ 359/315, 359/319, 244, 260, 578, 892; 385/88, 89, 385/90, 91, 92, 93; 257/443, 444, 458
See application file for complete search history.

(56) References Cited

U.S. PATENT DOCUMENTS

| | | | | |
|---|---|---|---|---|
| 5,408,319 A | | 4/1995 | Halbout et al. ............ 356/352 |
| 5,812,582 A | * | 9/1998 | Gilliland et al. ............ 372/50 |
| 5,814,871 A | * | 9/1998 | Furukawa et al. ........... 257/433 |
| 2003/0072009 A1 | * | 4/2003 | Domash et al. ............. 356/519 |
| 2003/0087121 A1 | | 5/2003 | Domash et al. ............. 428/641 |

FOREIGN PATENT DOCUMENTS

| | | |
|---|---|---|
| DE | 44 24 717 A1 | 1/1996 |
| DE | 44 24 717 | 1/1996 |
| EP | 0 901 170 | 3/1999 |
| WO | WO 00/23838 | 4/2000 |
| WO | WO 01/16637 | 3/2001 |

OTHER PUBLICATIONS

Augustine, et al., "Thermal–Optical Switching of a Silicon Based Interference Filter," *J. Appl. Phys.*, (1994), pp. 1875–1878, vol. 75(4).

* cited by examiner

*Primary Examiner*—Hung Xuan Dang
*Assistant Examiner*—Tuyen Tra
(74) *Attorney, Agent, or Firm*—Wilmer Cutler Pickering Hale and Dorr LLP

(57) ABSTRACT

An optoelectronic device including a header having an upper surface and including a plurality of conducting pins extending up through the upper surface; an optical device; a tunable optical filter, wherein the optical device and the tunable optical filter are arranged in a vertical stack mounted on and extending above the upper surface of the header and wherein the tunable optical filter is electrically connected to the plurality of conducting pins; and a cap affixed to the header and along with the header defining a sealed interior containing the optical device and the tunable optical filter, wherein the cap has a top surface with a window formed therein, and wherein the window is aligned with the tunable optical filter and the optical device.

28 Claims, 15 Drawing Sheets

PACKAGE FOR OPTICAL COMPONENTS

Under 35 U.S.C. §119(e)(1), this applications claims benefit of prior U.S. Provisional Application No. 60/335,178, entitled "Package for Tunable Filter Combined with Other Active Components," filed Nov. 28, 2001, and U.S. Provisional Application No. 60/394,500, entitled "Low Cost Hermetically Sealed Multi-Port Package for Optical and Opto-Electronic Devices," filed Jul. 9, 2002.

TECHNICAL FIELD

The invention relates generally to packages for optical components, including thermo-optically tunable thin-film filters as well as other active and passive optical devices.

BACKGROUND

Recently, a new device family has come into being, namely, thermo-optically tunable, thin-film filters. These devices, which are made from amorphous semiconductor materials, exploit what had previously been viewed as an undesirable property of amorphous silicon, namely, its large thermo-optic coefficient. The performance of these devices is based on trying to maximize thermo-optic tunability in thin-film interference structures, instead of trying to minimize it as is often the objective for conventional fixed filters.

FIG. 1 shows the basic device structure for the thermo-optically tunable thin film filter. The particular structure illustrated is a single cavity Fabry-Perot type filter 10. It includes a heater film 12 integrated into the optical interference design, and a Fabry-Perot cavity made of a pair of thin film mirrors 14(a) and 14(b) separated by a spacer cavity 16. In this example, heater film 12 is made of ZnO or polysilicon, so it is both electrically conductive and optically transparent at 1500 nm. Thin film mirrors 14(a) and 14(b) are alternating quarter wave pairs of high and low index films. The two materials are a-Si:H (n=3.67) and non-stoichiometric SiNx (n=1.77). Because of the large index contrast between a-Si and SiNx, a relatively small number of mirror pairs is required. Even 4 pairs yields reflectivity R=98.5% at the design wavelength, and 5 pairs yields R=99.6%. Cavity 16 is an integral number of half-waves, typically two to four, of amorphous silicon.

The amorphous thin films can be deposited by various physical vapor deposition techniques such as sputtering, or chemical vapor deposition techniques including plasma-enhanced enhanced chemical vapor deposition (PECVD). PECVD is a particularly flexible and homogeneous thin film process, and control of the basic deposition parameters such as plasma power, total gas pressure, hydrogen partial pressure, gas ratios, flow rates, and substrate temperature can be used to significantly modify film density and stoichiometry which in turn influence index, optical absorptivity, and thermo-optic coefficients. In addition, hydrogenation of the a-Si films can be used to quench dangling bonds and thereby decrease defect densities which, in turn, reduces infrared absorptivity. As a plasma based technique, PECVD offers the process variability needed to more easily produce dense, compliant films of several optically distinct but process-compatible materials, such as amorphous silicon and amorphous silicon nitride, with widely different indices. Transitions between materials can be accomplished by controlling gas mixtures, without breaking vacuum.

The finesse that is achievable with the thermo-optically tunable, thin film filters is illustrated by FIG. 2. In this case, the filter was a single cavity configuration using 6 mirror cycles and a fourth order spacer (4 half waves). The −3 dB width was 0.085 nm for a free spectral range of 388 nm and a finesse of approximately F=4,500.

The thermal tuning that is achievable is illustrated by FIG. 3. The configuration used an amorphous silicon spacer with dielectric mirrors (tantalum pentoxide high index and silicon dioxide low index layers, deposited by ion-assisted sputtering, R=98.5% mirror reflectivity). That structure was heated in an oven from 25 C. to 229 C. The tuning was approximately 15 nm or $d\lambda/dT=0.08$ nm/K.

Finally, the benefit of constructing a tunable filter with all-PECVD films using amorphous silicon not only for the spacer but also for the mirror high index layers is illustrated in FIG. 4. This filter, with 4 period mirrors, incorporated an electrically conductive ZnO layer for heating internal to the film stack, which is able to achieve much higher local film temperatures than if it the heater was separate from the film stack. The tuning range in this example was 37 nm.

Further details about these new structures can be found in U.S. patent application Ser. No. 10/174,503 filed Jun. 17, 2002, entitled "Index Tunable Thin Film Interference Coatings;" and U.S. patent application Ser. No. 10/211,970 filed Aug. 2, 2002, entitled "Tunable Optical Instruments," both of which are incorporated herein by reference.

SUMMARY

In general, in one aspect the invention features an optoelectronic device including a header having an upper surface and including a plurality of conducting pins extending up through the upper surface; an optical device; a tunable optical filter; and a cap affixed to the header and along with the header defining a sealed interior containing the optical device and the tunable optical filter. The optical device and the tunable optical filter are arranged in a vertical stack mounted on and extending above the upper surface of the header; the tunable optical filter is electrically connected to the conducting pins; and the cap has a top surface with a window formed therein and aligned with the vertically stacked tunable optical filter and optical device.

In general, in another aspect, the invention features an optoelectronic device including a header having an upper surface and including a plurality of conducting pins extending up through the upper surface; an optical device supported on the top surface of the header with a major surface thereof substantially parallel to the upper surface of the header; and a cap affixed to the header and along with the header defining a sealed interior containing the optical device. The cap has a top surface with a first window formed therein and the header has a second window formed therein.

Different embodiments include one or more of the following features. The header and cap are a Transistor Outline (TO) package. The tunable optical filter is a thermo-optically tunable thin-film filter. The optical device is an emitter (LED) or a detector. The optoelectronic device also includes a standoff structure mounted on the top surface of the header and defining a first surface on which the optical device is mounted and a second surface on which the tunable optical filter is mounted. The cap on the header forms a hermetically sealed interior and may include a collar holding a fiber collimator or other fiber optics. The optoelectronic device also includes a substrate with the filter formed on one surface thereof and the optical device mounted on an opposite surface thereof.

Various embodiments of the invention have one or more of the following advantages. They provide a low-cost, small-footprint package. They provide for "free space" tunable filters that do not rely on waveguide effects, but rather treat collimated beams in free space to achieve wavelength filtering. Packaging can use established, standard enclosures (e.g. TO packages) that have been modified appropriately. In that event, the packaging approach can take advantage of well-established assembly techniques and widely available, inexpensive enclosures. This will result in drastically reducing the cost of assembly and materials, as compared to using custom packaging designs. In addition, it lends itself to easily producing sealed packages (optionally, hermetically sealed) that have electrical feed-throughs and one or more transparent windows through which light travels. Moreover, eliminating the need for optical fiber feed-throughs also dramatically reduces the cost of packaging and enhances the reliability of the overall system.

Hermetic packages of the types disclosed herein are desirable for optical components due to the strict reliability requirements of optical communications systems. Current hermetic multi-port optical device packaging technologies include butterfly, mini-DIL, and innumerable machined aluminum packages of custom design. To maintain hermeticity, most packages used for pass through optics employ laser welding for seam sealing, which is both complex and expensive to implement in production. The simplest packages of this type often cost upwards of $20.00 each, while the more complex can approach hundreds of dollars.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
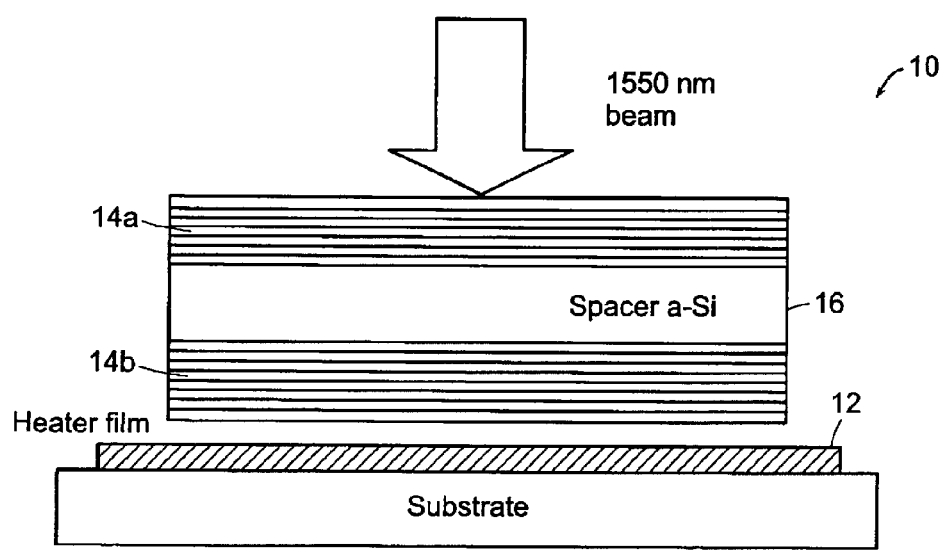
FIG. 1 shows the basic device structure of a thermo-optically tunable thin film filter.
Figure 2:
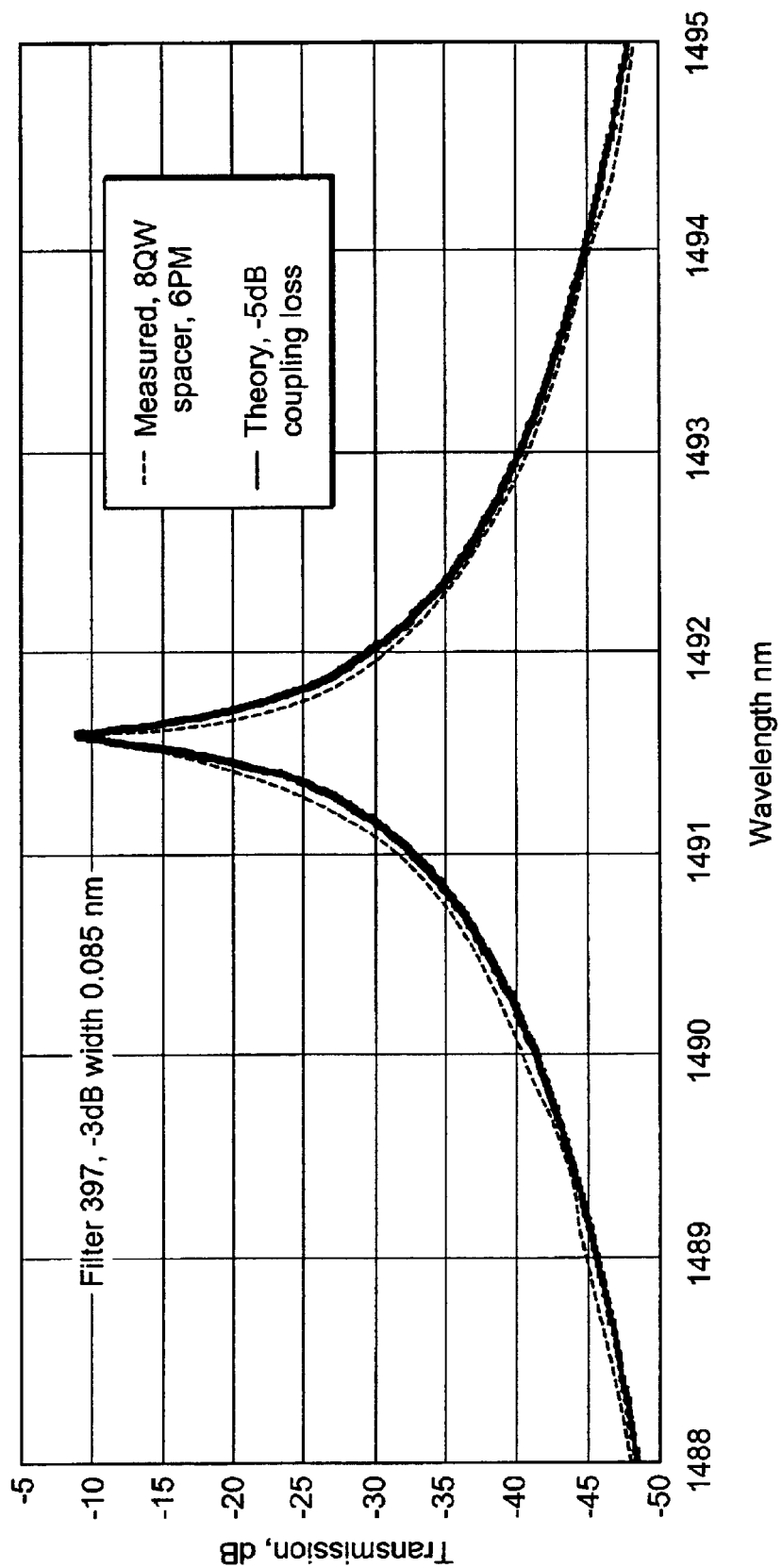
FIG. 2 is a plot of filter transmission characteristics showing the finesses of a single cavity, thermo-optically tunable, thin-film filter.
Figure 3:
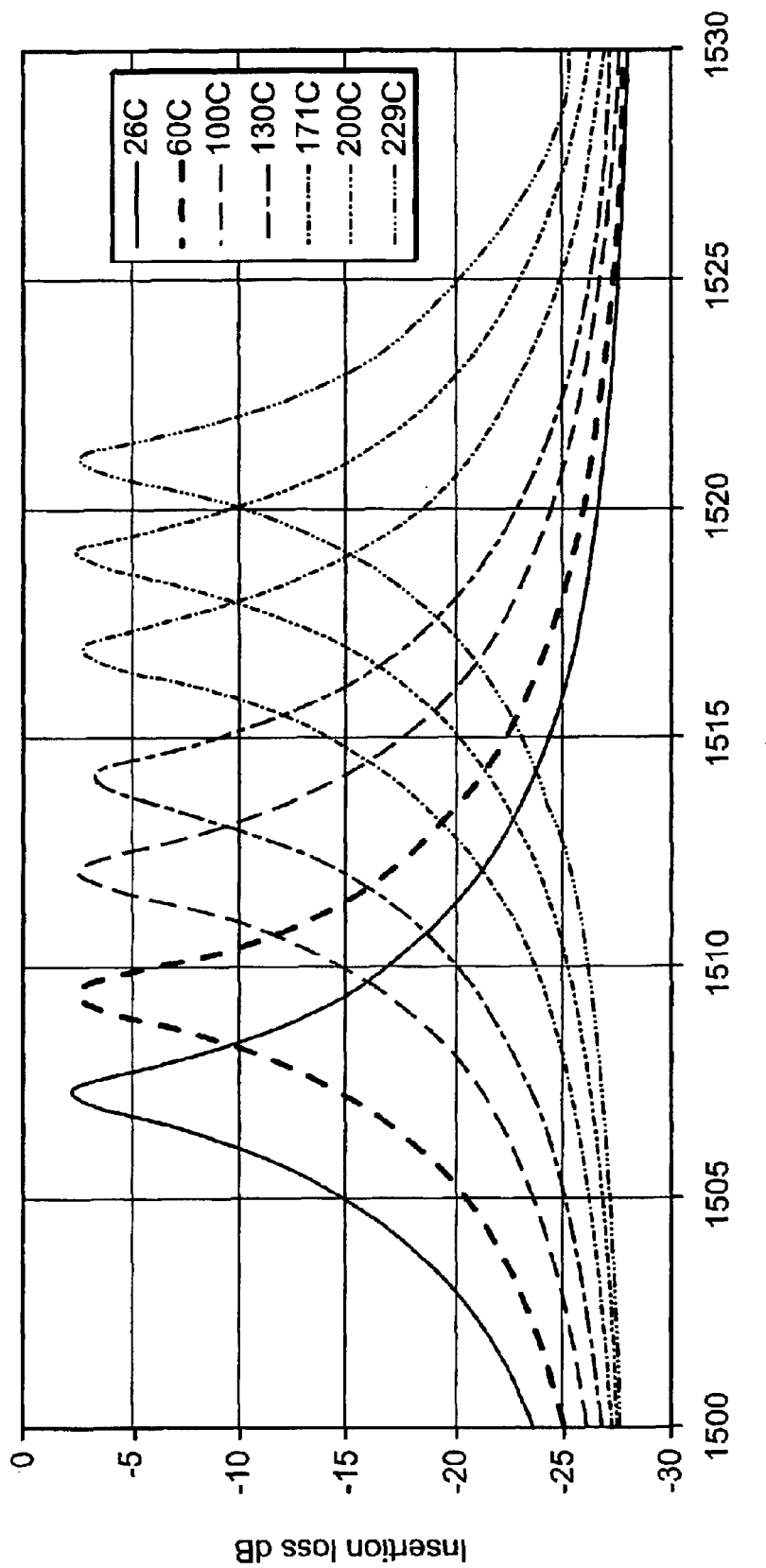
FIG. 3 presents multiple plots of filter transmission characteristics showing the tuning range of a filter with thermo-optic spacer and dielectric mirrors.
Figure 4:
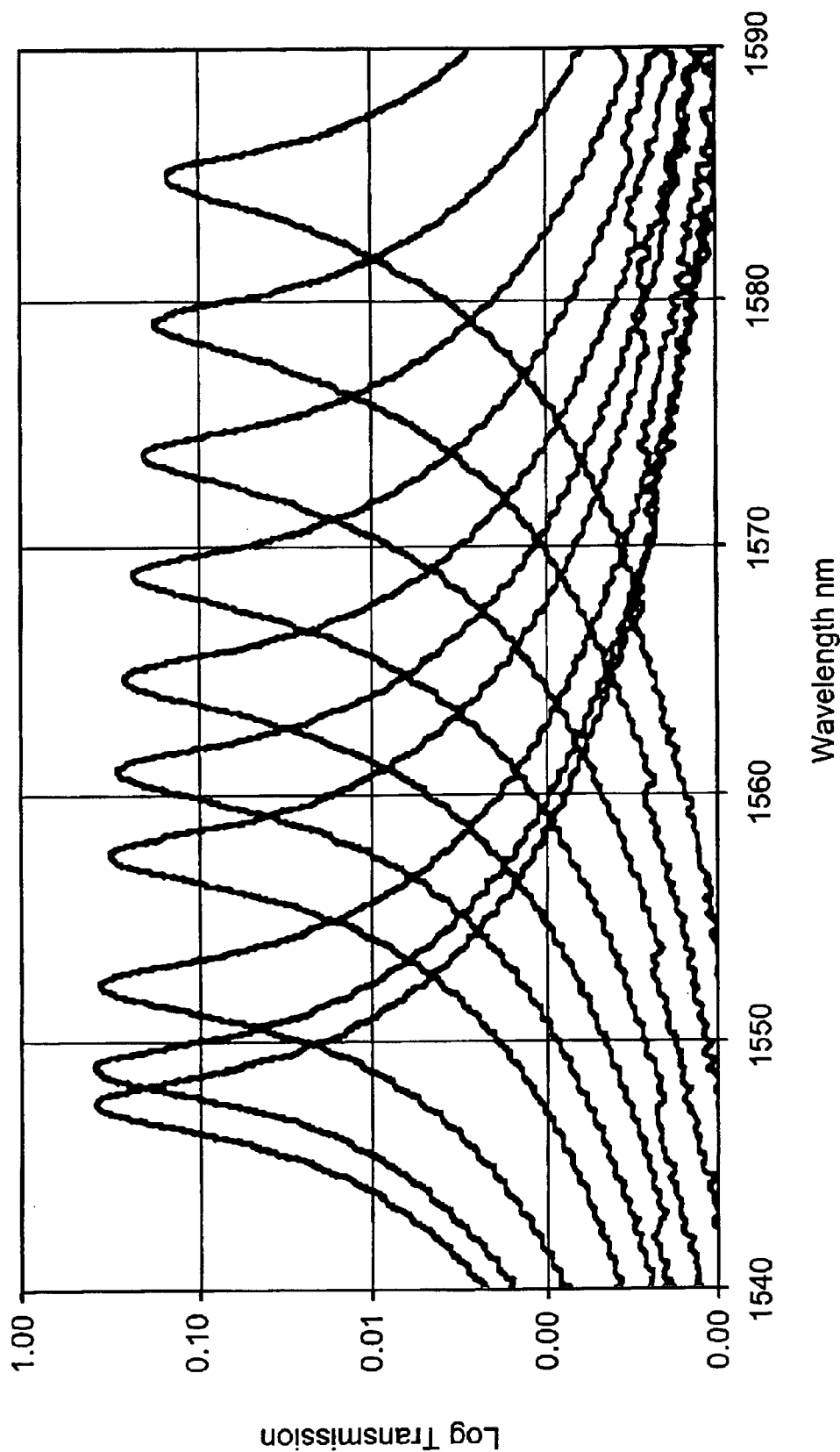
FIG. 4 presents multiple plots of filter transmission characteristics showing the tuning range of an all-PECVD filter, including a-Si:H high index layers and spacer, SiNx low index layers, and 4 period mirrors.
Figure 5A:
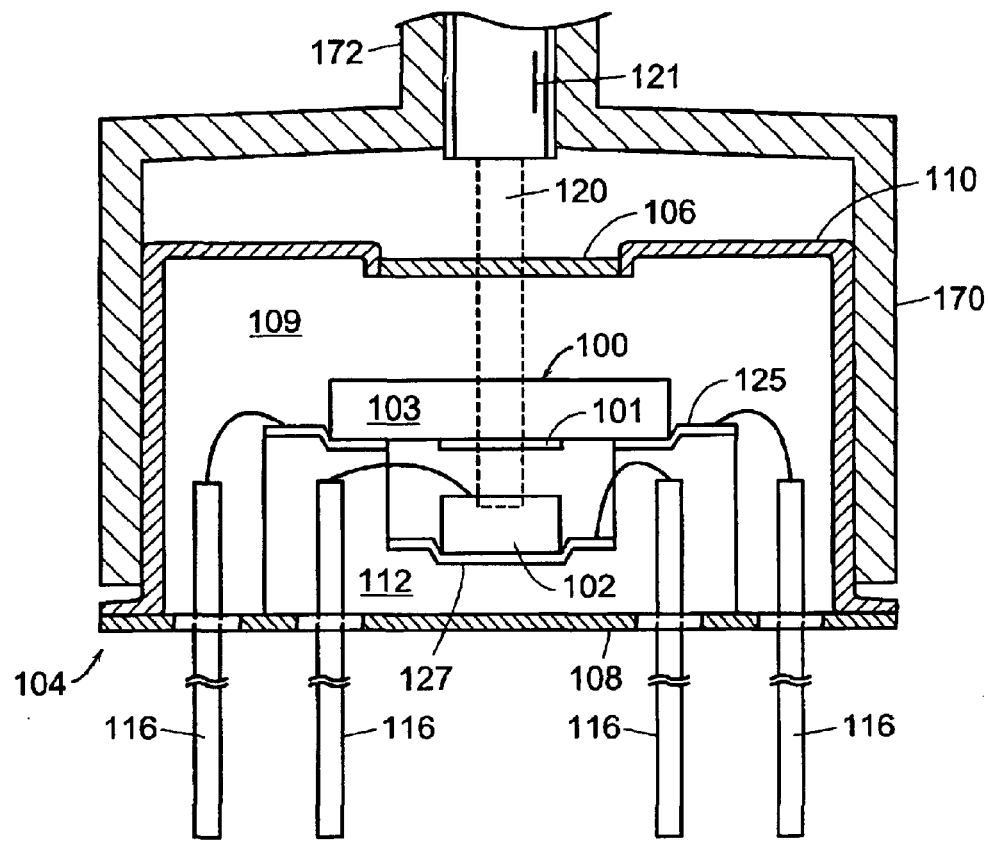
FIG. 5A is a cross-sectional cutaway view showing the core elements of one family of embodiments.

Referring to FIG. 5A, one family of embodiments involves packaging a free-space tunable optical filter component 100 together with one or more passive and/or active optical/optoelectronic components 102 in a "stack up" format inside a package 104 with an optical access window 106 through which a free-space optical beam can pass. Package 104 includes a header 108 with a cap 110 mounted thereon and forming a sealed interior cavity. A stand-off element 112 is affixed to header 108 and a plurality of electrical pins 116 come up through header 108 to enable electrical connections to be made to tunable filter component 100 and to other optoelectrical components inside of package 104. Stand-off element 112 holds tunable filter component 100 and opto-electronics 102 in a vertically arranged stack with the major plane of filter component 100 arranged substantially parallel to the upper mounting surface of header 108. In operation, a light beam 120 from a optical fiber 121 passes through window 106 into the interior of package 104 where it then passes through tunable filter component 100. A filtered beam exiting the other side of tunable filter component 100 then impinges on optoelectronics 102.

Stand-off element 112 is made out of an electrically insulating material such as a ceramic (e.g. alumina or aluminum nitride). This element suspends tunable filter 100 at a fixed, well-controlled distance above optoelectronics 102 (e.g. a PIN detector or LED emitter). Additionally, conductive traces (or contact pads) 125 and 127 may be defined on this stand-off for the purpose of contacting and interconnect. In the described embodiment, filter component 100 includes a substrate 103 with a tunable thin-film filter element 101 formed in its downward facing surface. This is an example of flip-chip mounting according to which the device is flipped over and mounted onto the stand-off to facilitate making electrical connections to the metal traces formed on the substrate surfaces.

Using passive alignment guides or reference marks, the tunable filter and the optoelectronic components may be accurately aligned in the x-y plane where typical requirements for free-space elements is on the order of 10 microns, and may be accurately placed along the z-axis. Such assembly, which may be accomplished using standard chip-mounting equipment—and possibly done in large volumes on an automated line, is dramatically more cost-effective than "silicon micro-bench" type assemblies typically used for multi-element optical communications assemblies. In addition, it is significantly more resilient mechanically because all components lay flat on stand-off or package surfaces rather than be arrayed as vertically oriented elements over a horizontal surface.

Again referring to FIG. 5A, a cover 170 with an integrally formed collar 172 located in its top fits onto cap 110 of package 104. Cover 170 holds optical fiber 121 (which may include collimating or focusing optics at its end) within collar 172 and properly aligns it with respect to window 106 within package 104. The collimating optics can take various forms including a GRIN (gradient index lens) or a ball lens. Similarly, the focusing optics can also take various forms.

Figure 5B:
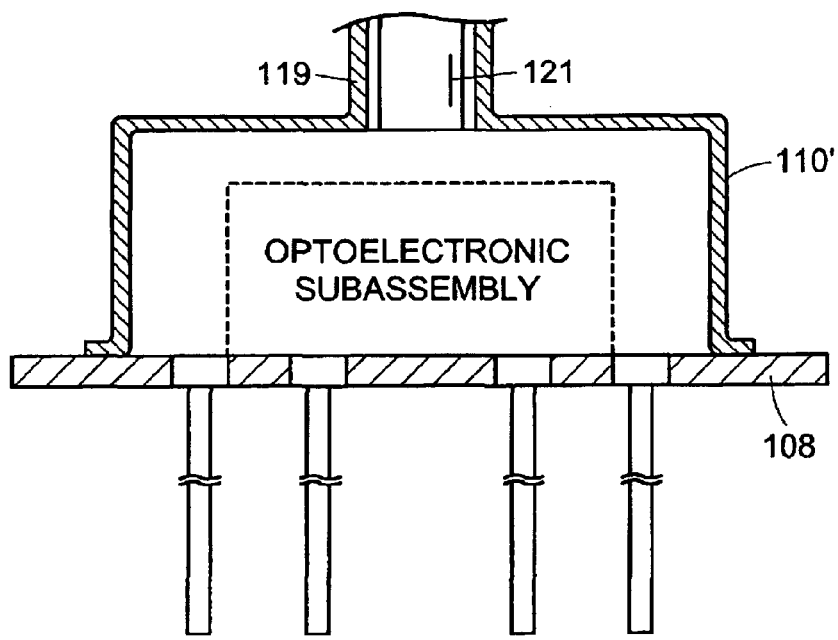
FIG. 5B illustrates an alternative design for the cap on the package.

Alternatively, as shown in FIG. 5B, a modified cap 110' can be provided which includes a collar 119 integrally formed therein. Optical fiber 121 is sealed in collar 119 and serves as the window into the package. This does away with the need of providing a separate cover as shown in FIG. 5A.

Figure 6:
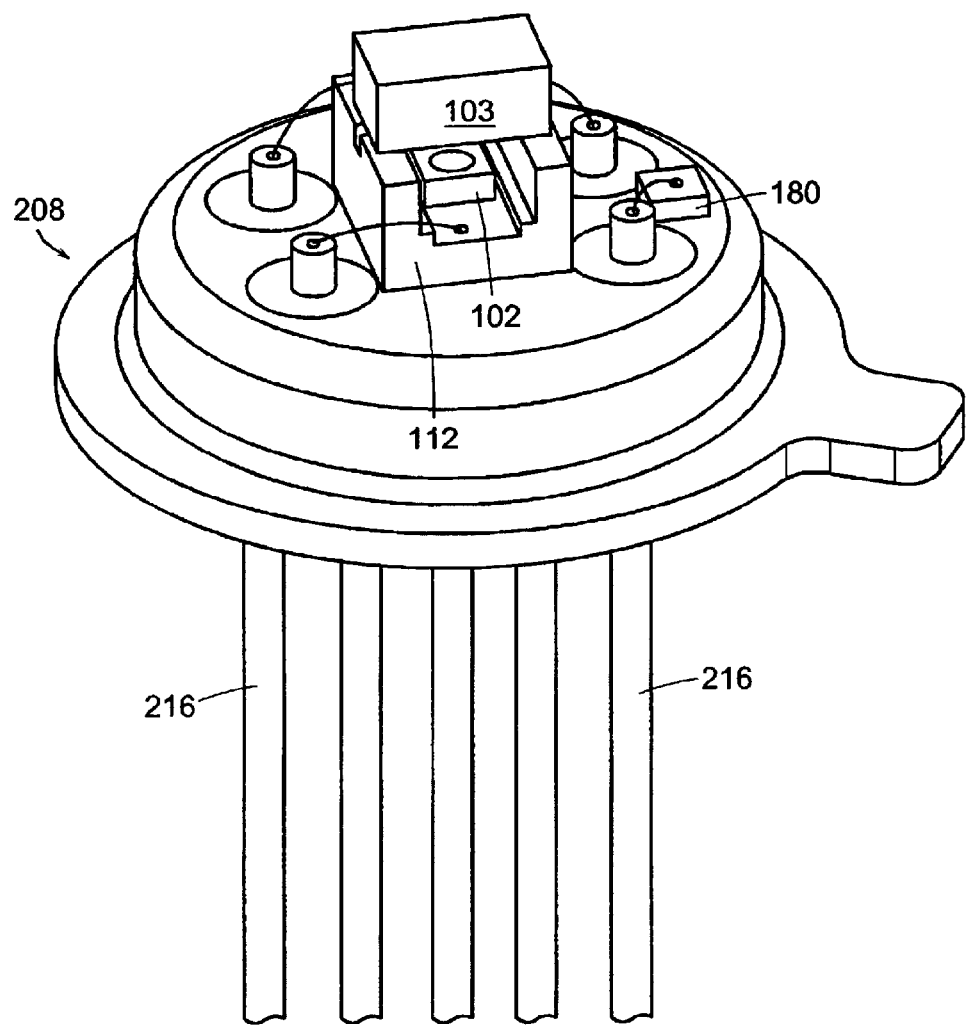
FIG. 6 show a modified TO package embodiment.

Referring to FIG. 6, an example of a commonly available package that can be used is a TO ("Transistor Outline") style package which includes a round metallic can 210 (see FIG. 7A) mounted on a header 208. Header 208 has multiple integral conducting pins ("feet") 216 extending through it and hermetically sealed within the pass-throughs using a solder glass. These conducting pins provide a way to electrically address or connect with the internal optoelectronics and associated elements. When fully assembled, the pins are connected to corresponding metallic pads on the enclosed optoelectronics by wires.

The optoelectronic components shown in the embodiment of FIG. 6 are the same as those that are shown in FIG. 5. In addition, mounted on header 208 is a temperature sensor (e.g. thermistor) that is used to monitor the temperature of the package to aid in the operation of the thermo-optically tunable thin film filter.

Figure 7A:
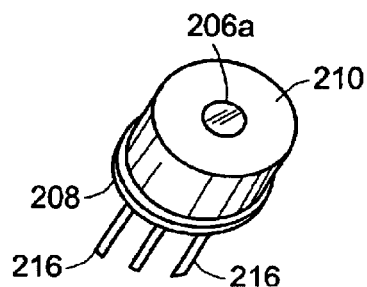
FIGS. 7A, 7B and 7C show modified TO packages with different types of windows in the top of the can.
Figure 7B:
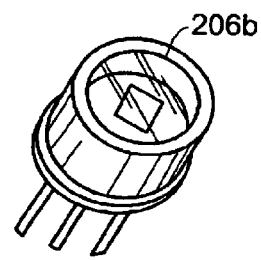
Figure 7C:
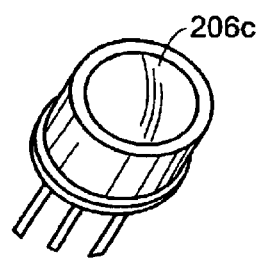

Referring to FIGS. 7A–C, the TO package lends itself particularly well to optical devices that require incident light perpendicular to the device plane, such as Fabry-Perot filters. Can 210 is modified by including in its top surface a window which may be one of several different designs. For example, it could be a ball lens 206(a) (see FIG. 7A); it could be a flat window 206(b) of the type that is used for single detectors (see, FIG. 7B), or it could be an integrated lens 206(c) (see FIG. 7C). The cost of materials in such a package is less than one dollar, which is dramatically lower than "butterfly"-type packages with fiber feedthroughs that are widely used in the industry. In addition, manual or automated equipment for assembling, wirebonding, and sealing such a package is readily available and comparatively low-cost.

Figure 7D:
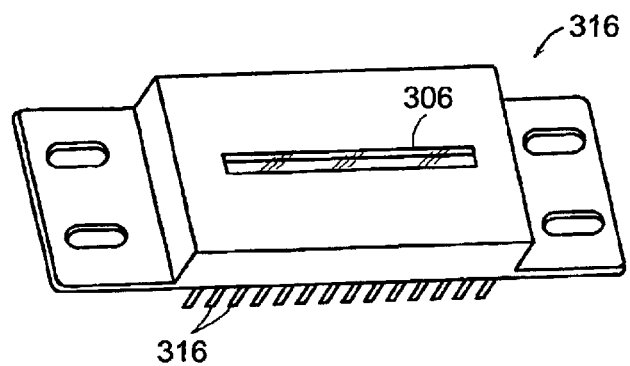
FIG. 7D shows a dual-inline package embodiment.

Referring to FIG. 7D, an example of another commonly available package that can be used is a dual-inline package 300 with a top window 306 of the type used for linear detector arrays. The dual-inline package also includes a header that defines a planar surface onto which the optoelectronic elements are stacked vertically, as described above. Pins 316 extend out of the bottom side of the header and provide a means by which one can electronically connect to the optoelectronic devices within the sealed package. Window 306 provides a transparent region in the top of the package through which an optical beam can reach the enclosed optoelectronic devices.

Multi-Port Package

Figure 8A:
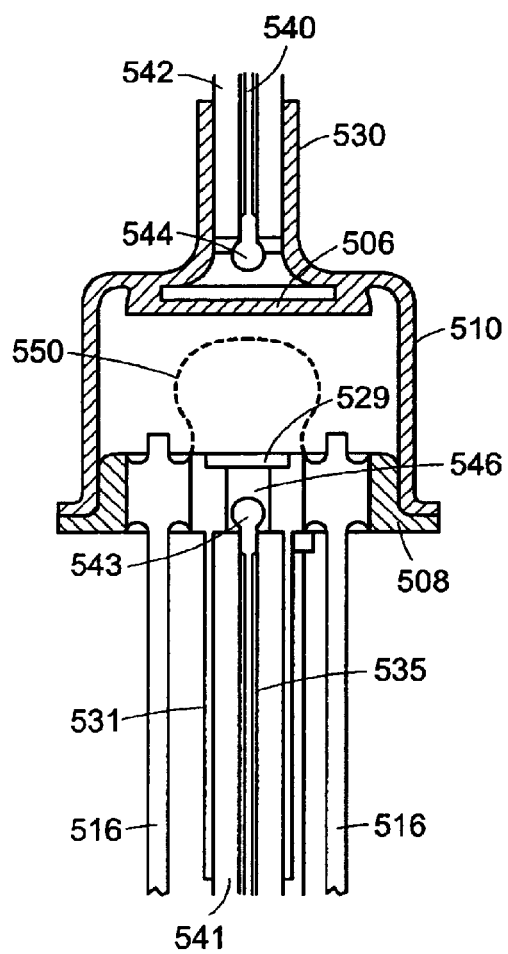
FIGS. 8A and 8B shows a multi-port embodiment with axially aligned input and output ports at the top and bottom, respectively.
Figure 8B:
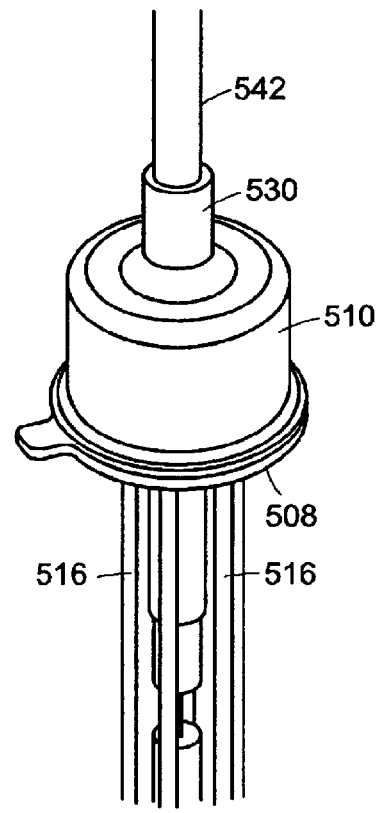

FIGS. 8A and 8B show a further modification of the design described above. It is a generic configuration for a 2-port, TO package and includes an integrated feed-through which allows optical signals to pass through optoelectronic circuitry inside of the package.

In this example, the modified TO package, like the one previously described, includes a metal cap 510 sealed onto a header 508. Within header 508 there is a plurality of conducting pins 516 extending up through the header. In the top of cap 510, there is a window 506 with its perimeter sealed to the metal of the cap. An integrally formed, metal ferrule 530 extends upward from the main body of cap 510 and surrounds window 506. Ferrule 530 holds an optical fiber 540 enclosed in a sleeve 542. A ball lens 544 is attached to the end of optical fiber 540 and adjacent to window 506. Ball lens 544 collimates the light coming out of the optical fiber before it passes into the modified TO package. Header 508 includes a thru-hole 546 formed at its center with a window 529 at the top end of this thru-hole and sealed in a recess formed in the upper surface of header 508. A ferrule 531 extends down away from the bottom of header 508 and aligned with thru-hole 546. Ferrule 531 holds another optical fiber 535 enclosed in a sleeve 541. A ball lens 543 is affixed to the top of optical fiber adjacent to window 529.

This arrangement defines an optical path through the center of the package along its longitudinal axis. Any one of a number of different combinations of optoelectronic devices 550 can be mounted on the header inside the package and in the optical path.

Figure 9A:
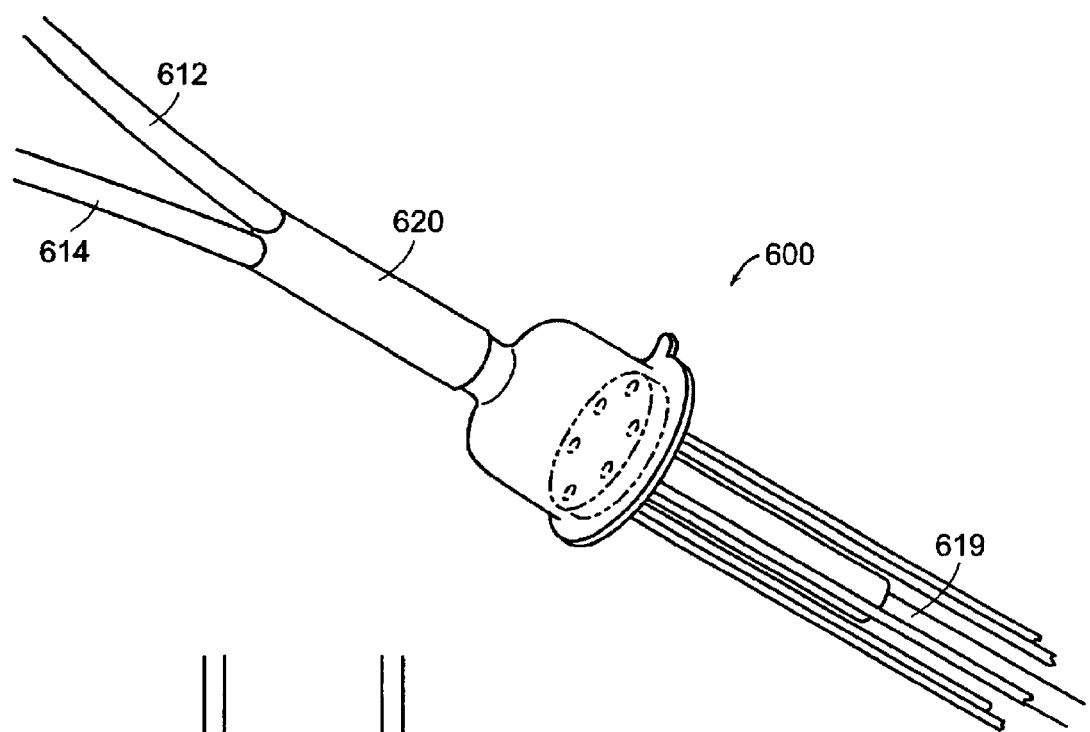
FIGS. 9A and 9B show a three-port device which is an optical add/drop multiplexer.
Figure 9B:
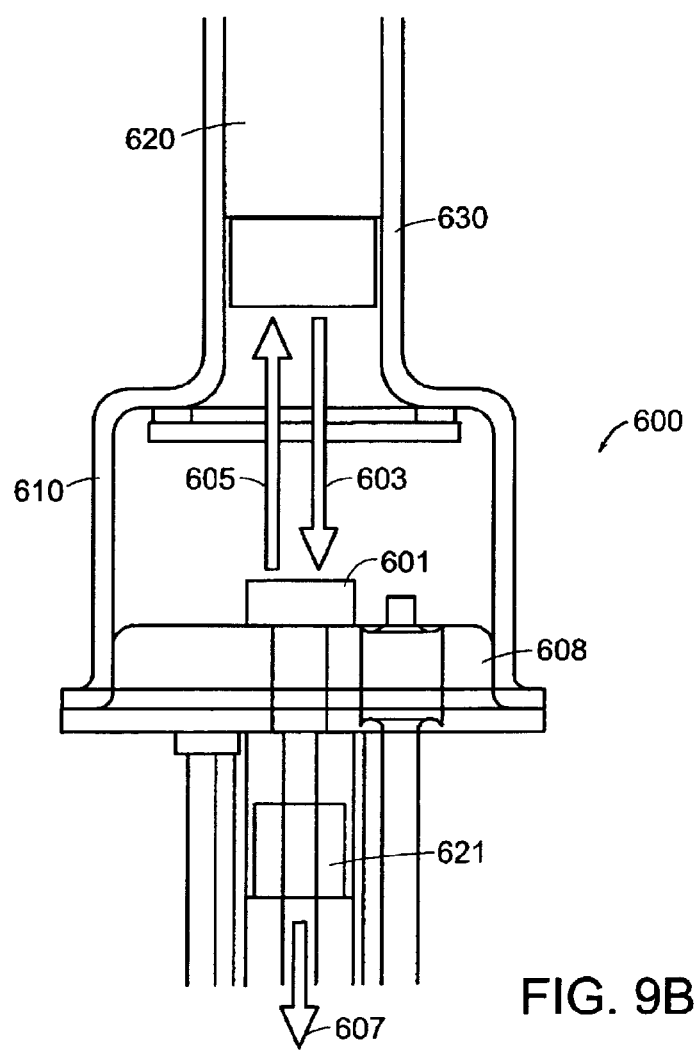

An example of a three-port configuration is shown in FIG. 9, is an optical add/drop multiplexer 600. It includes a thermo-optically tunable thin-film filter 601 mounted on a header 608 and inclined at a slight angle (e.g. <5°) relative to the upper surface of the header. A dual fiber collimator 620 (e.g. a GRIN lens) is positioned within a ferrule 630 extending out of the top of cap 610 with two optical fibers 612 and 614 connected to one end of the dual fiber collimator. Optical fiber 612 represents an input channel and optical fiber 614 represents an output channel. At the other end of the package is a third optical fiber 619, aligned with a thru-hole similar to what was described in connection with the device shown in FIG. 8A. Thermo-optically tunable thin-film filter 601 and dual-fiber collimator 620 are aligned relative to each other so that an incoming light beam 603 from optical fiber 612 impinges on tunable optical filter 601 at an angle that is slightly less than perpendicular its surface.

Incoming beam 603 represents a number of different channels, each at a different wavelength. A characteristic of tunable thin-film filter 601 is that it passes a selectable one of the wavelengths on to fiber 619. The remainder of the channels (i.e., wavelengths) that are outside of that narrow transmitted passband are reflected off tunable thin-film filter 601 and back towards dual fiber collimator 620 as a reflected beam 605. The relative alignment of tunable thin-film filter 601 and collimator 620 is such that the reflected wavelengths enter collimator 620 and are directed into output fiber 614. A transmitted beam 607 passes out into optical fiber 619. In this mode of operation, the device acts as a drop multiplexer, i.e., it drops or pulls off a selected one of the multiple channels of the input optical signal.

Alternatively, if the optical signal of the appropriate wavelength is input through fiber 621, the device functions as an optical add multiplexer, i.e., it adds the new channel to the multi-channel signal that is passing through the device.

Figure 15:
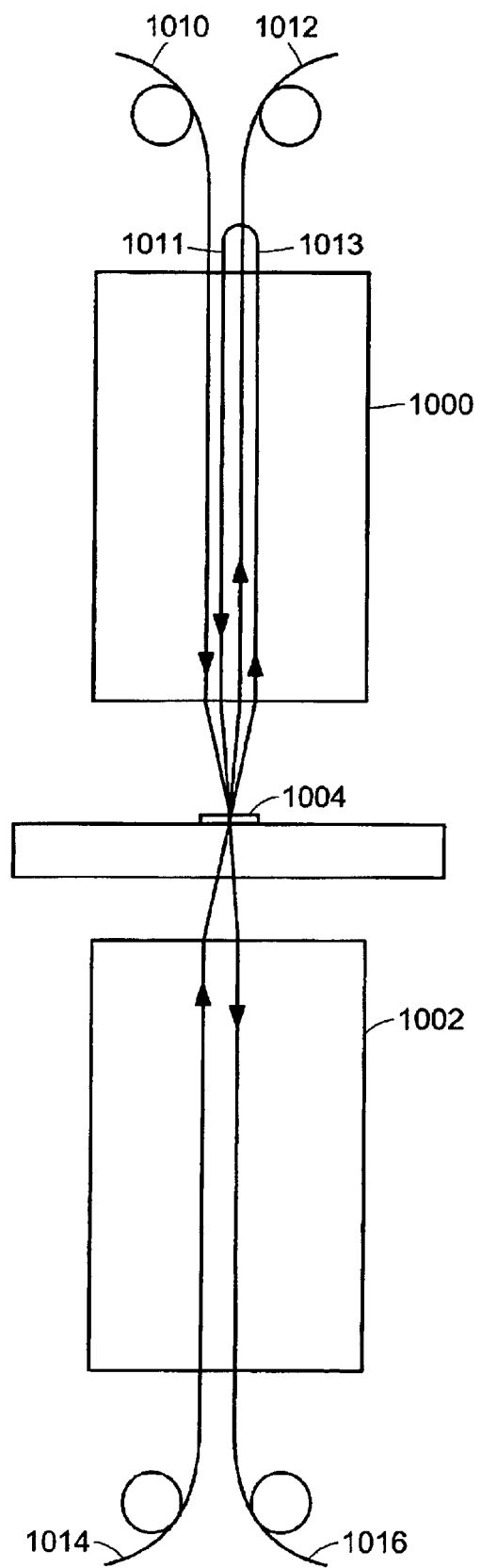
FIG. 15 shows another multi-port embodiment.

Referring to FIG. 15, another multi-port configuration utilizes multi-port input and multi-port output optics as well as add/drop optics to allow a more efficient package design. This performs the functions of two or more three-port packages in a single six-plus port design. This is desirable due both to space and power consumption considerations. Both add and drop processes occur in this single assembly, permitted by the use of differing angles of incidence for the add cycle and the drop cycle, yet still utilizing the same position on the filter surface. This avoids interference effects which would otherwise result in degradation of both the transmitted and reflected signals. Add/drop, add/add, or drop/drop configurations may be attained in this package configuration, dependent only on input/output arrangement.

The disclosed embodiment includes two GRIN lenses 1000 and 1002 (or other comparable optical elements). There are four optical fibers connected to lens 1000, symmetrically arrayed across the input face of the lens. As is well known, light beams that are displaced from the central axis of the lens come out of the other end of the lens at an angle determined by the displacement of the optical fiber from the central axis. This principle is used to advantage in the following way.

Connected to lens 1000 are four optical fibers 1010, 1011, 1012, and 1013 linearly arranged in symmetrical fashion about the central axis of the lens. In other words, optical fibers 1010 and 1013 are the two outer fibers each equally distant from the axis of lens 1000 and optical fibers 1011 and 1012 are the two inner fibers also equally distant from the central axis of the lens. Optical fiber 1010 supplies a multi-channel optical input signal to lens 1000, which in turn delivers that signal to a tunable filter 1004 at an angle Θ relative to its normal direction. Tunable filter 1004 passes a selectable one of the channels of the input signal through to lens 1002, which supplies it to a drop fiber 1016 placed at the appropriate location on the face of lens 1002. The rest of input signal reflects off of tunable filter 1004, back through lens 1000, and into optical fiber 1013. Optical fiber 1013 is connected to optical fiber 1011 so as to deliver its received signal bask to lens 1000 at the location of optical fiber 1011. This returned optical signal is sent back to tunable filter 1004 but this time at a smaller angle relative to its normal. When it reaches tunable filter, since the selected channel has already been removed, all of it is reflected back to lens 1000, which delivers that reflected signal to output optical fiber 1012.

Input fiber 1014, which carries an ADD signal at the frequency of the dropped channel, supplies an optical signal to the backside of tunable filter 1004 and at an angle such that when it is transmitted by filter 1004 it combines with the reflected signal that is delivered to output fiber 1012.

Other Implementations

Various applications require different combinations of tunable filters, optics, and other active devices in small packages. FIGS. 10A–D show four general categories of possible combinations of tunable filters with other active optoelectronics, though this list of examples is not exhaustive.

Figure 10A:
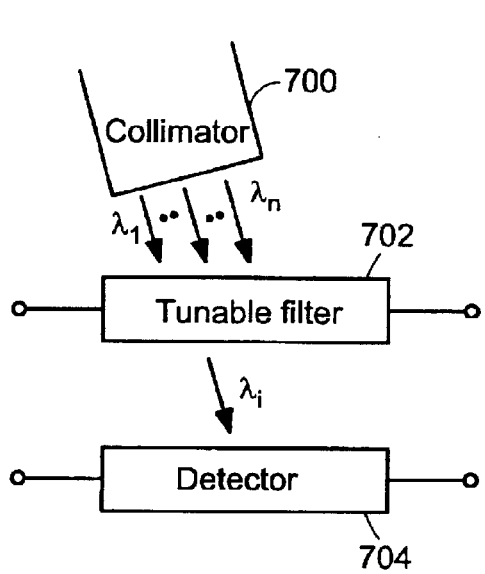
FIGS. 10A–D show four general categories of optical component configurations.

The combination illustrated in FIG. 10A includes input optics, a tunable filter 702, and a detector 704. Input optics 700, which my include a collimator, delivers an optical signal that is made up of multiple wavelengths to tunable filter 702, which allows a selectable one of the multiple wavelengths of the optical signal to pass through to detector 704. Typical applications for this system include spectral power monitoring and single-channel detection or monitoring. In the case of spectral power monitoring, tunable filter 704 is operated to scan back and forth over the wavelength range of interest and detector 704 measures the powers of the different wavelengths within the optical signal. In the case of single-channel detection or monitoring, tunable filter 702 is tuned to a single wavelength and detector 704 monitors the signal in that band—a "tunable detector" or "tunable receiver"). In any event, the system is typically not designed to return rejected wavelengths to output optics.

Figure 10B:
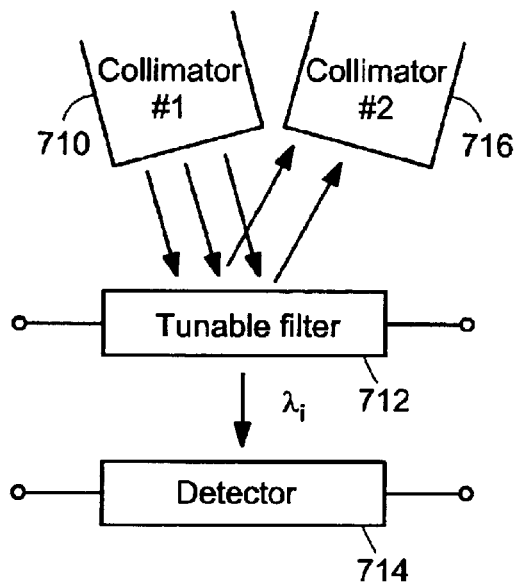

The combination illustrated in FIG. 10B, includes input optics 710, a tunable filter 712, a detector 714, and output optics 716. A typical application of such a system is an "optical drop" according to which tunable filter 712 admits a single channel to detector 714, and the wavelengths rejected by tunable filter 712 reflect into output optics 716, such as a collimator. Such a configuration would be useful in a flexible communications network in which each location can dynamically select which communications channel (i.e., wavelength) to detect.

Figure 10C:
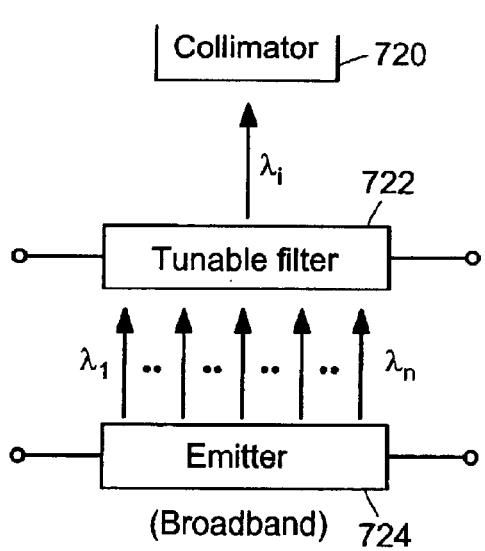

The combination illustrated in FIG. 10C includes a broadband light source or emitter 720, a tunable filter 722, and output optics 726. Broadband light source 720, such as a light-emitting diode (LED), is used in conjunction with tunable filter 722 to create a tunable narrowband light source. When tunable filter 722 is a thermo-optically tunable thin film filter, such as was described above, it becomes possible to create a low-cost tunable source for measurement applications or low-cost optical networks.

Figure 10D:
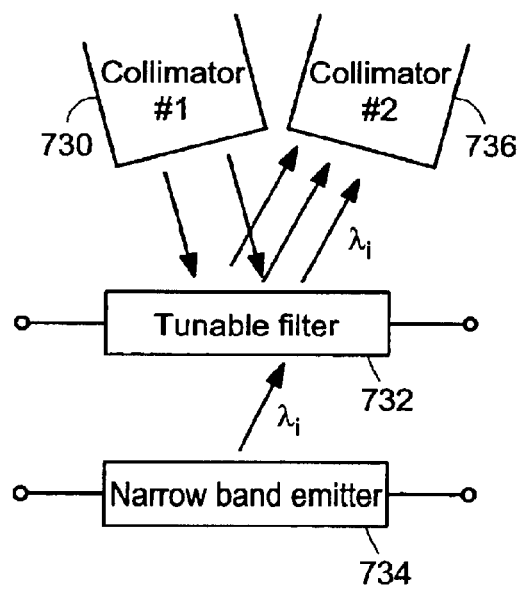

The combination illustrated in FIG. 10D includes input optics 730, a tunable filter 732, an emitter 734, and output optics 736. Emitter 734 may be either a broadband, fixed emitter or a tunable, narrowband emitter, such as a tunable vertical cavity surface emitting laser which is "added" into an optical stream by way of a tunable filter. In this instance, tunable filter 732 admits the new wavelength along the same path as the reflected ("through") wavelengths. Such a system could work in conjunction with the system shown in FIG. 10B to dynamically add and drop wavelengths in a network, or it could be used as a "universal spare" transmitter that can be set to any wavelength needed.

There may be a broad range of applications that require similar systems, where the active optical elements besides the tunable filter are detectors, emitters, or other optical elements used to measure or treat light. With the packaging ideas presented herein, it now becomes possible to construct such systems in a low-cost, small form factor manner to make their widespread application feasible.

Beam Alignment

Return loss is the ratio of the amplitude of the reflected wave to the amplitude of the incident wave. In optical applications this is measured in −dB, and for a component the reflected power is defined as the total reflection from all surfaces within a component which are conducted back through the optical fiber. Virtually all optical systems place restrictions on the amount of RL for reasons of stability.

Optical assemblies that are manufactured with a Return Loss (RL) specification are routinely designed and toleranced both in components and assembly such that a calculated angle of incidence is achieved between the component surface(s) and the source(s). This angle is calculated to provide sufficiently High RL to meet customer specifications. However, since the performance of most optical components degrades as a function of angle (due primarily to polarization dependence), there is a trade-off, between the amount of buffer needed to cover mechanical tolerance stack-ups and the required device performance. This level of precision in both device and tooling is prohibitively expensive and extraordinarily difficult to design, maintain and manufacture.

An alternative to this process of specifying tight tolerances on the components has been to utilize costly and cumbersome tip/tilt action to achieve the desired alignment. In this case, RL is actively monitored while automated equipment tips, tilts and rotates the components relative to the source until the performance requirements are satisfied and then the component is fixed in that position. This process, however, requires highly precise automated equipment that is very expensive.

A new alignment method which achieves the required RL parameters, which can be implemented with off-the-shelf tooling, and which is much less expensive will now be described with the aid of FIG. 11 and FIGS. 12A and B. This new method is also an active alignment process according to which the orientation of the source is changed to optimize a monitored RL. The method works on loosely toleranced parts such as those described herein, though it is applicable to any axially aligned system.

Figure 11:
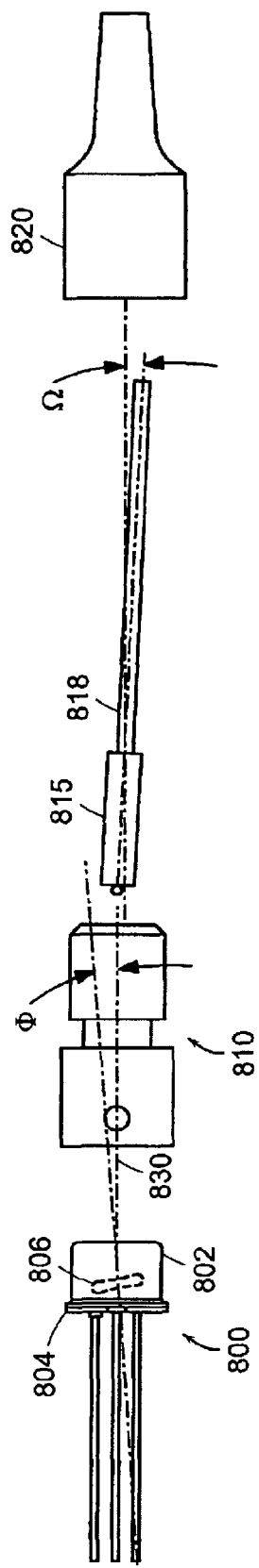
FIG. 11 shows an exploded view of an approach to aligning the fiber/collimator onto the package containing the opto-electronic components.
Figure 12A:
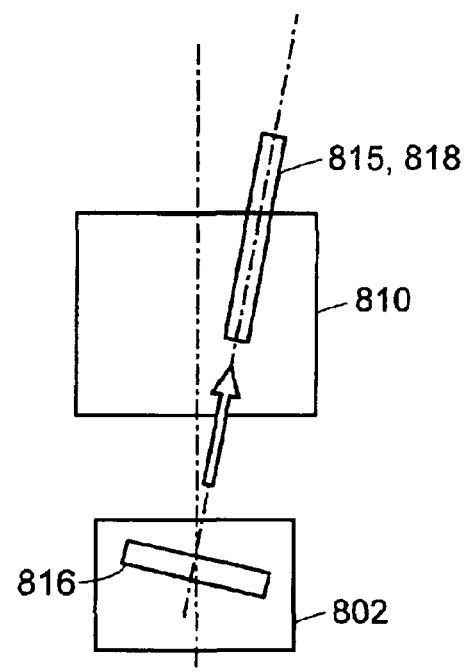
FIGS. 12A and 12B illustrate the alignment procedure for optimizing return loss.
Figure 12B:
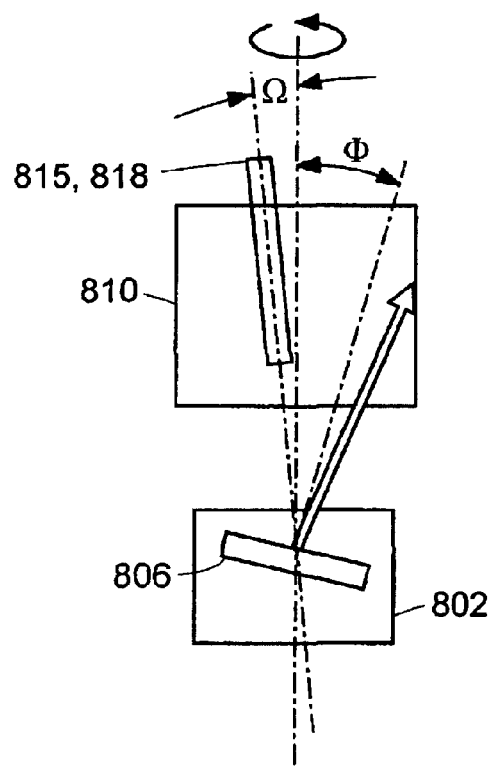

Referring first to FIG. 11, a packaging structure which is designed to implement the improved alignment procedure includes a modified TO package 800 with a cap 801 attached to a header 804. On header 804 there is mounted a tunable thin-film optical filter 806 (or an optical device to which the input fiber is to be aligned). In the described embodiment, tunable filter 806 is mounted at a small angle ($\Phi$) relative to the underlying top surface of header 804 (or stated differently, so that its normal is at a small angle ($\Phi$) relative to the longitudinal axis 830 of the package). A sleeve assembly 810 which holds an optical fiber 818 and a collimator 815 slides over and loosely fits onto cap 802 of the package, thereby roughly aligning the fiber with the window in the top of the cap. Until sleeve assembly 810 is anchored to the cap (e.g by means of an epoxy or screws in the side of the sleeve), sleeve assembly 810 is capable of being rotated on the cap about longitudinal axis 830 of the package. A cover 820 slides over and covers the sleeve once the sleeve is properly oriented.

Sleeve assembly 810 holds the fiber and collimator at a small angle ($\Omega$) relative to its axis of rotation (which for the package illustrated is also the longitudinal axis of the cap/package). As illustrate by FIGS. 12A and B, by rotating sleeve assembly 810 about its axis of rotation while it is fitted onto cap 802, the angle between the optical beam and the normal to the surface of the optical component sweeps through all angles $\Phi-\Omega$ through $\Phi+\Omega$. For example, if the collimator and the normal to the component are parallel to each other (i.e., $\Phi=\Omega$), but off angle from the axis of rotation by 2 degrees, then the angle of incidence may be varied using this method from 0–4 degrees. This angular differential may be either designed or a byproduct of assembly/manufacture.

By actively monitoring the input to and output from the optical fiber during this rotation operation, the desired high Return Loss can be achieved within tenths of a dB, minimizing any degradation due to higher than necessary angle of incidence.

If the sleeve fits loosely on the cap, there can also be an XY alignment step during which the sleeve is moved in a plane parallel to the plane of the header to find its optimum location as a function of device performance. Similarly, since there is a "waist" to the beam coming from the collimator, where all rays are presumed to be near parallel, this is where the active optical component surface is ideally placed. But in view of the low divergence of the beam, this is very loosely toleranced, that is, both filter performance and RL are typically quite insensitive to Z position. So alignment in this dimension (i.e., the Z axis) can be satisfactorily achieved by using a simple mechanical stop in the sleeve that sets the Z position of the collimator relative to the optical component.

A full alignment procedure involves the following sequence of steps while monitoring the measured RL. First there is a course adjustment in the Z-direction. Then, RL is optimized by rotating the sleeve. Next, further optimization of device performance is achieved by aligning in the XY plane. And finally, there is a further fine adjustment in the Z direction.

Stacking Buildup Methods

As mentioned above, an advantage of some of the embodiments described here is that they permit the use of Z-axis buildup methods of fabrication. The Z-axis buildup methods are low cost and include but are not limited to: (1) multilevel (e.g. stepped) stand-offs such as ceramics used to space apart components along the z-axis and align them on the x-y plane; (2) flip-chip mounting of optical/optoelectronic and other chips onto passive substrates and/or substrates on which other optoelectronic elements are fabricated; (3) pre-mounting of components onto substrates/stand-offs and assembly into a package using passive alignment of these substrates; and (4) mounting of substrates or components directly onto electrical pins inside the package.

Assembly Guides Used

Figure 13A:
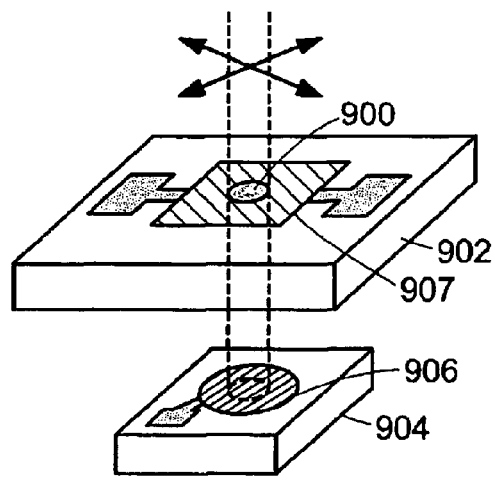
FIGS. 13A–C illustrate alternative assembly techniques that can be used.
Figure 13B:
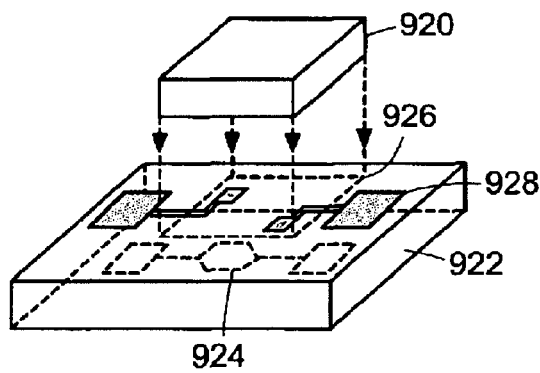
Figure 13C:
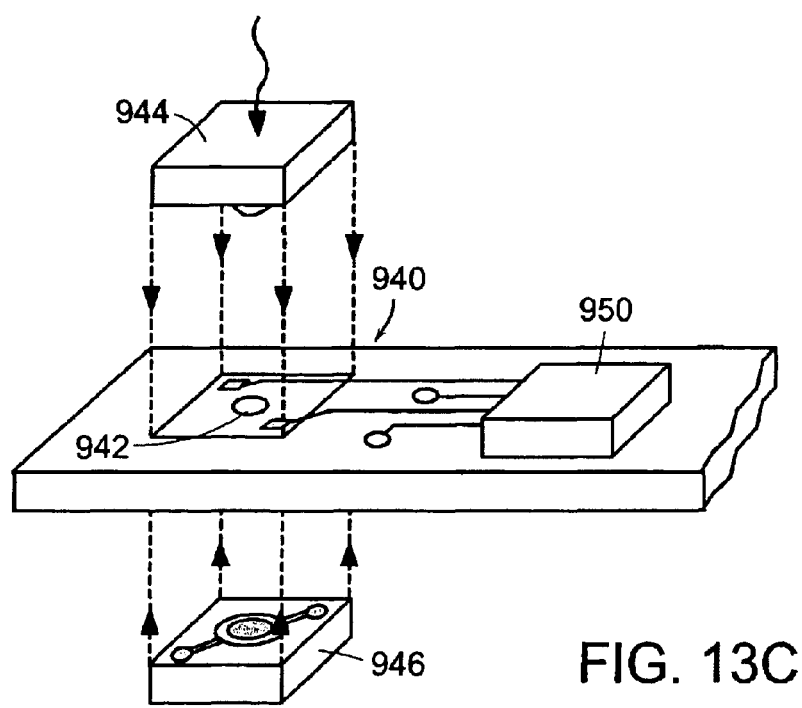

As illustrated in FIGS. 13A–C, several patterning methods are available to minimize the assembly precision and effort required. For example, referring first to FIG. 13A, a mask or aperture 900 can be patterned on one component (e.g. tunable filter 902) and then the other component (e.g. a detector 904) can be designed to have a significantly larger active area 906 to account for passive alignment tolerances. In addition, referring to FIG. 13B, one can use standardized surface-mount technology (SMT) assembly methods and machines to obtain high alignment accuracies, possibly with the aid of optical alignment guides that are interpreted by SMT machinery. In that case, for example, a detector or emitter chip 920 can be flip-chip mounted onto a back surface of a substrate 922 that has a tunable, thin-film optical filter 924 formed on its front surface. There can be photo-lithographically defined alignment guides 926 and contacts 928 formed on the back surface of substrate 922 to facilitate alignment and contact to detector or emitter chip 920. Alternatively, one can use intermediate masks on substrates or optics to align individual optical/optoelectronic components. Also, one can build hybrid structures as illustrated by FIG. 13C. For example, a substrate or board 940 holding other circuitry or connectors 950 (such as drive circuits or read circuits) can be provided with an optical thru-hole 942 to enable optical communication between components that are to be mounted on both sides of substrate 940 (e.g. a tunable optical filter chip 944 that is flip-chip mounted on one side of substrate 940 and a detector or emitter chip 946 that is flip-chip mounted on the other side of substrate 940).

Figure 14A:
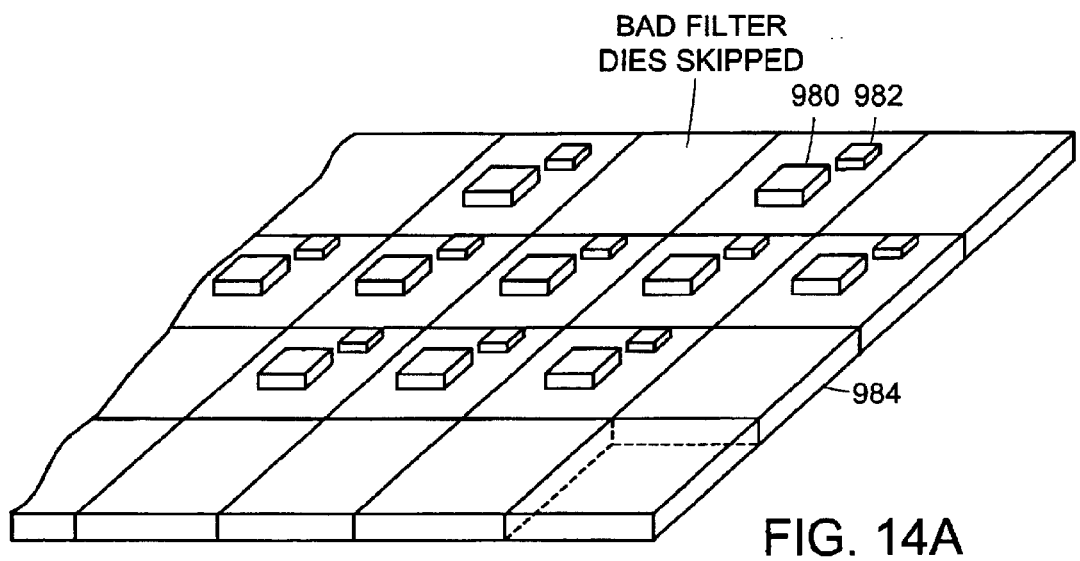
FIGS. 14A and B illustrate techniques for making multiple die on a single substrate.

In addition, large-volume assembly of components based on conventional electronics methods (SMT, for instance) may be used to build optoelectronic assemblies in "sheets" before separating and packaging them. An example of such an assembly process is shown in FIGS. 14A and B, where a detector element 980 and a thermistor element 982 are mounted on the reverse side of a tunable thin film filter substrate 984. Several hundred or thousand such subassemblies may be automatically assembled and a solder reflow (or wirebond) process applied before the thin film filter wafer is diced and the resulting subassemblies are packaged.

Figure 14B:
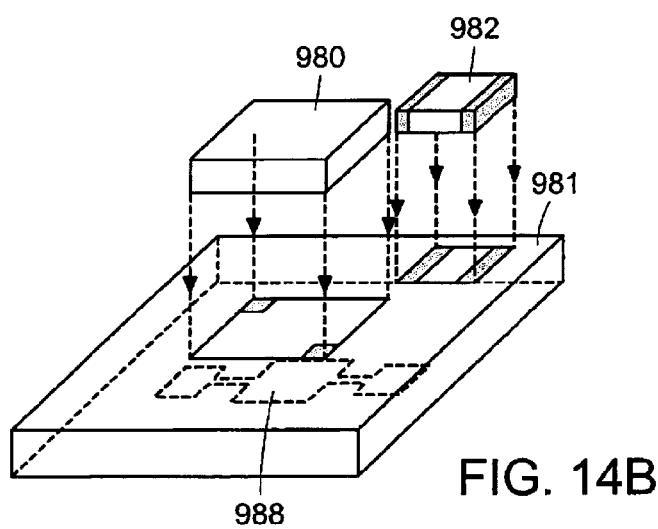

FIG. 14B illustrates one method of building such assemblies. Substrate 984 is patterned to accept detector element 980, thermistor element 982, a tunable filter element 988, and possibly other components, and is then diced. Certain pieces of the substrate are then stacked to create stand-off elements with patterned metal traces.

Optics Used

The optical configurations that may be used with the packages described above include, but are not limited to: (1) inbound optical signals, outbound optical signals, or both in-bound and outbound optical signals; (2) collimated or focused beams, though preferably collimated in the case of the tunable filter; (3) using only external optics only, a combination of external and internal optics, or internal, package-integrated optics only; (4) passive optical coatings used on external optics, on the transparent window to the package, or on internal elements such as substrates for the purpose of anti-reflection coatings, high-reflection coatings, or selective wavelength filtering; and (5) optical elements such as single- or dual-fiber collimators used external to the package, lenses integrated into the package itself, or micro-optical elements used in the stack-up of components internal to the package.

Aperture Plate

In the embodiments that use a thermo-optically tunable thin-film filter, the heating element in the tunable thin film filter should typically be made as small as possible for at least two reasons. First, the speed of the device will be faster for a smaller heater because a smaller thermal mass needs to be heated and cooled. Second, the device can run at a lower power because the temperature of the tunable element is proportional to the power density. For a given required maximum temperature, and therefore a given required power density, the smaller the heater, the lower the required input power.

However, the drawback to having a small heating element is the difficulty created in trying to optically align it to a free space, collimated beam. All of the light transmitted through the tunable filter must pass through the heated portion of the device. Any light transmitted through an unheated part of the filter, or through an un-filtered part of the device will contain unwanted wavelengths, and will add unwanted noise to the desired signal.

To realize very low cost packaging, alignment should be as easy, passive, and automated as possible. One approach to achieving this is by integrating into the device a layer that blocks any light from being transmitted through any part of the device except the heated portion of the tunable filter. In its simplest form, this would be a metal layer 907 with a small aperture aligned to the heating element, as shown in FIG. 13A. In this case, the alignment only has to be good enough to ensure that some part of the collimated beam hits the aperture. The rest of the collimated beam can hit outside the heater area with no consequence because this light will be reflected, not transmitted. Therefore, the light-blocking layer with an aperture ("aperture layer") enables a relatively small heater. Also, the aperture should be small compared to the heater area. This will ensure that temperature non-uniformities near the edges of the heating element are minimized, leading to a narrower peak.

The aperture layer should be thick enough to have enough reflectivity to reject the required amount of light. However, if it is too thick it can add unwanted stress to the film stack and/or contribute detrimental thermal properties to the device by conducting away too much heat. If the aperture layer does conduct away too much heat, it can lead to a non-uniform temperature distribution in the aperture, and will require more input power to the heater to reach a given temperature. Also, the aperture layer needs to be able to withstand the possibly high temperatures required to tune the device. Some common metals that could be used for this purpose include: Al, Ag, Cu, Au, Pd, Pt, Ni. Fe, Cr, W and Ti. Ideally, the material would have a high k value at the wavelength of interest (e.g. 1550 nm), a high melting temperature since metals will typically soften and creep at a fraction of their melting temperature, a low thermal conductivity, and a low thermal mass (i.e., mass density x specific heat) so the aperture layer does not conduct away too much heat. Note that non-metallic materials are also an option for the aperture layer.

Free-Space Filters:

The types of tunable filters which can be used in the embodiments described herein are "free-space" filters that admit beams of light that may be collimated and filter out a specific wavelength or sets of wavelengths for transmission or reflection. These filters are referred to as "free-space" filters because the optical beams to be filtered are unguided except for input and output optics which extract them from and insert them into waveguides such as optical fibers. A number of such tunable optical filter devices are known in the art. These include, but are not limited to:

Tunable, thin film optical filters, including the thermo-optically tunable thin film filters mentioned above, which have great advantages in terms of performance, cost, and reliability and fit this packaging format exceptionally well.

Microelectromechanical systems (MEMS)-based Fabry-Perot filters using two or more dielectric mirrors that are moved together or apart for tuning purposes; this includes both conventional silicon-based MEMS and those devices based on polymer films or other materials.

Holographic or grating waveguide-coupled filters where in-plane patterns are used to create a filter for light traveling along the z-axis (or used to deflect a particular wavelength or set of wavelengths off-axis).

Piezo-electric Fabry-Perot based on Piezo thin films. Many other free-space filters that exist or are under development will benefit from the packaging approach described in this disclosure.

It is to be understood that while the invention has been described through the use of detailed embodiments thereof, the foregoing description is intended to illustrate and not limit the scope of the invention, which is defined by the scope of the following claims. Thus, other aspects, advantages, and modifications are within the scope of the following claims.

What is claimed is:

1. An optoelectronic device comprising:
a header having an upper surface and including a plurality of conducting pins extending up through the upper surface;
an optical device;
a tunable optical filter, wherein said optical device and said tunable optical filter are arranged in a vertical stack affixed to the upper surface of the header and wherein said tunable optical filter is electrically connected to a set of said plurality of conducting pins; and
a cap affixed to the header and along with the header defining a sealed interior containing the optical device and the tunable optical filter, wherein said cap has a top surface with a window formed therein, said window aligned with the tunable optical filter and the optical device.

2. The optoelectronic device of claim 1 wherein the header and cap are a Transistor Outline (TO) package.

3. The optoelectronic device of claim 1 wherein the tunable optical filter is a thermo-optically tunable thin-film optical filter.

4. The optoelectronic device of claim 3 wherein the optical device is an emitter (LED).

5. The optoelectronic device of claim 3 wherein the optical device is a detector.

6. The optoelectronic device of claim 3 further comprising a standoff structure mounted on the top surface of the header, wherein the standoff structure defines a first surface on which the optical device is mounted and a second surface on which the tunable optical filter is mounted.

7. The optoelectronic device of claim 3 wherein the cap on the header forms a hermetically sealed interior.

8. The optoelectronic device of claim 3 wherein the cap includes a collar holding fiber coupling optics.

9. The optoelectronic device of claim 3 further comprising a substrate with the tunable optical filter formed on one surface thereof and the optical device mounted on an opposite surface thereof.

10. The optoelectronic device of claim 3 wherein the cap and the header define an internal cavity in which the optical filter is present, said optoelectronic device further comprising:
 a first optical fiber external to the internal cavity and aligned with the first window; and
 a second optical fiber external to the internal cavity, aligned with the second window, and next to the first optical fiber.

11. The optoelectronic device of claim 3 in which there is an optical path extending from the window to the optical device, and wherein the optical filter lies along the optical path between the window and the optical device.

12. The optoelectronic device of claim 3 wherein the optical device is a broadband light emitter.

13. The optoelectronic device of claim 3 optical device is a narrowband light emitter.

14. An optoelectronic device comprising:
 a header having an upper surface and including a plurality of conducting pins extending up through the upper surface;
 a thermally tunable optical filter supported on the top surface of the header, wherein said optical device is electrically connected to a set of said plurality of conducting pins; and
 a cap affixed to the header and along with the header defining a sealed interior containing the thermally tunable optical filter, wherein said cap has a top surface with a first window formed therein and the header has a second window formed therein and wherein the thermally tunable optical filter lies along an optical path extending between the first and second windows.

15. The optoelectronic device of claim 14 wherein the header and cap are a Transistor Outline (TO) package.

16. The optoelectronic device of claim 14 wherein the thermally tunable optical filter is a thermo-optically tunable thin-film optical filter.

17. The optoelectronic device of claim 16 wherein the cap on the header forms a hermetically sealed interior.

18. The optoelectronic device of claim 16 wherein the cap includes a collar holding a fiber collimator wherein the window is a lens.

19. The optoelectronic device of claim 16 wherein the cap includes a ferrule extending upward from its top surface and providing a bore for holding an optical feed.

20. The optoelectronic device of claim 16 wherein the cap and the header define an internal cavity in which the optical filter is present, said optoelectronic device further comprising:
 a first optical fiber external to the internal cavity and aligned with the first window; and
 a second optical fiber external to the internal cavity and aligned with the second window.

21. The optoelectronic device of claim 20 wherein the cap has a ferrule extending therefrom and aligned with the first window, said ferrule holding the first optical fiber.

22. The optoelectronic device of claim 21 wherein the header has a ferrule extending therefore and aligned with the second window, said ferrule holding the second optical fiber.

23. The optoelectronic device of claim 20 further comprising a third optical fiber external to the internal cavity, aligned with the first window, and next to the first optical fiber.

24. The optoelectronic device of claim 23 further comprising a collimator aligned between the first window on one side and the first and third optical fibers in another side.

25. The optoelectronic device of claim 24 wherein said collimator is a dual fiber collimator.

26. The optoelectronic device of claim 23 wherein the combination of the optical filter optoelectronic device functions as an optical add/drop multiplexer.

27. The optoelectronic device of claim 16 further comprising an optoelectronic circuit in the internal cavity, said optoelectronic circuit including said tunable optical filter.

28. The optoelectronic device of claim 27 wherein the tunable optical filter has a major surface with a normal that is inclined slightly relative to said optical path.

* * * * *